United States Patent
Yu et al.

(10) Patent No.: US 9,402,534 B2
(45) Date of Patent: Aug. 2, 2016

(54) TWO DIMENSIONAL FORWARD SCANNING PROBE

(71) Applicant: Novartis AG, Basel (CH)

(72) Inventors: Lingfeng Yu, Lake Forest, CA (US); Xiaoyu Yu, San Diego, CA (US); Jack Auld, Laguna Niguel, CA (US)

(73) Assignee: NOVARTIS AG, Basel (CH)

(*) Notice: Subject to any disclaimer, the term of this patent is extended or adjusted under 35 U.S.C. 154(b) by 244 days.

(21) Appl. No.: 14/133,504

(22) Filed: Dec. 18, 2013

(65) Prior Publication Data

US 2015/0164311 A1    Jun. 18, 2015

(51) Int. Cl.
*A61B 5/05* (2006.01)
*A61B 1/07* (2006.01)
*A61B 1/00* (2006.01)
*A61B 5/00* (2006.01)

(52) U.S. Cl.
CPC .............. *A61B 1/07* (2013.01); *A61B 1/00112* (2013.01); *A61B 1/00172* (2013.01); *A61B 1/00188* (2013.01); *A61B 5/0062* (2013.01); *A61B 5/0066* (2013.01); *A61B 5/0084* (2013.01)

(58) Field of Classification Search
CPC ............. A61B 5/0066; A61B 1/00172; A61B 2017/00539; A61B 2017/00544; A61B 5/6848; A61B 5/0084; A61B 1/05; A61B 1/0016
See application file for complete search history.

(56) References Cited

U.S. PATENT DOCUMENTS

| | | | |
|---|---|---|---|
| 7,261,687 B2 | 8/2007 | Yang | |
| 7,364,543 B2 | 4/2008 | Yang | |
| 7,591,783 B2 * | 9/2009 | Boulais | A61B 1/00059 600/139 |
| 8,118,732 B2 * | 2/2012 | Banik | A61B 1/00059 600/117 |
| 2001/0036002 A1 | 11/2001 | Tearney et al. | |
| 2005/0234345 A1 | 10/2005 | Yang | |
| 2009/0187098 A1 * | 7/2009 | Makower | A61B 17/12022 600/424 |
| 2012/0190921 A1 | 7/2012 | Yadlowsky et al. | |
| 2012/0191078 A1 | 7/2012 | Yadlowsky et al. | |
| 2012/0245569 A1 | 9/2012 | Papac et al. | |
| 2012/0330101 A1 | 12/2012 | Brennan et al. | |
| 2013/0144278 A1 | 6/2013 | Papac et al. | |
| 2013/0158392 A1 | 6/2013 | Papac et al. | |
| 2013/0158393 A1 | 6/2013 | Papac et al. | |
| 2013/0331709 A1 | 12/2013 | Le et al. | |

OTHER PUBLICATIONS

International Search Report and Written Opinion issued for PCT/US2014/069127 dated Mar. 6, 2015, 9 pgs.
Wu et al., "Paired-angle-rotation scanning optical coherence tomography forward-imaging probe", Optics Letters, vol. 31, No. 9, May 1, 2006, pp. 1265-1267.
Yaqoob et al., "Methods and application areas of endoscopic optical coherence tomography", Journal of Biomedical Optics, vol. 11(6), Nov./Dec. 2006, 19 pgs.

* cited by examiner

*Primary Examiner* — Joel Lamprecht
(74) *Attorney, Agent, or Firm* — S. Brannon Latimer (57) ABSTRACT

An optical scanning probe comprises a handle to receive a light beam from a light guide; a cannula, extending from a distal end of the handle; a fiber, positioned partially inside the handle and partially inside the cannula, to guide the received light beam toward a distal end of the cannula; a rotating scanner, rotatably positioned at least partially inside the cannula and configured to house a proximal portion of the fiber; and a deflecting scanner, movably coupled to a distal end of the rotating scanner, configured to deflect a distal portion of the fiber, wherein the distal portion of the fiber is configured to emit and scan the guided light in a target region.

27 Claims, 8 Drawing Sheets

TWO DIMENSIONAL FORWARD SCANNING PROBE

TECHNICAL FIELD

This patent document relates to scanning probes. More precisely, this patent document relates to forward scanning probes capable of scanning in two dimensions.

BACKGROUND

Forward scanning optical probes are used in various applications, including imaging, diagnostic and surgical devices. Forward scanning optical probes, or for short, scanning probes, emit light at a distal end of the scanning probe and scan the emitted light across a target region. In imaging applications, these scanning probes also collect the light, reflected from the target region, and deliver the collected light to an imaging system.

The scanning probes utilize scanning mechanisms, examples of which include microelectromechanical scanners and piezoelectric scanners. However, implementing these scanning mechanisms within the narrow confines of a scanning probe for medical applications, such as within a cannula of a medical endoprobe with a diameter of less than 1 mm, proved to be particularly challenging.

The scanning can be performed along a one dimensional (1D) line, or along two dimensional (2D) patterns. One design to achieve a 2D scanning capability includes a "paired angle rotation scanning" (PARS) probe. Such PARS probes have been suggested, e.g., for Optical Coherence Tomography (OCT) imaging applications. A PARS probe utilizes a pair of angle-cut GRIN lenses, one rotated by an outer cannula and the other counter-rotated in the opposite direction by an inner cannula, housed within the outer cannula. The synchronized counter-rotation of the two GRIN lenses can deflect and scan an OCT probe beam along a variety of 2D scanning patterns in the target region ahead, or forward, of the probe tip. It proved to be possible to design PARS probes with an outer diameter of 1.65 mm. However, PARS designs have their own limitations, as follows.

1. The two counter-rotating cannulas of a PARS probe require challengingly high precision manufacturing.

2. Implementing some of the widely used scanning patterns can be another challenge. For example, to achieve a 1D linear scan, the two cannulas have to be counter-rotated at exactly the same angular velocity in opposite directions. Even a small difference, or mismatch, of the angular velocities disadvantageously results in a non-linear scan pattern, typically not even a closed loop.

Another example is the moving of the scanning beam to a specific point, e.g., to start a new scan. Doing so also requires that the two GRIN lenses are synchronously rotated by the same angle in opposite directions. If the rotations of the two GRIN lenses are not synchronized with high enough precision and end up moving the scanning beam to a shifted position, then the shift of the coordinates of the specific point needs to be compensated by a shift of the calibration of the imaging system.

Some systems attempt to improve the precision of the counter-rotation, but those systems typically introduce additional complexities into the already tight space of the probe.

SUMMARY

To address the above challenges, embodiments described in this patent document include an optical scanning probe, comprising a handle, configured to receive a light beam from a light guide; a cannula, extending from a distal end of the handle; a fiber, positioned partially inside the handle and partially inside the cannula, configured to guide the received light beam toward a distal end of the cannula; a rotating scanner, rotatably positioned at least partially inside the cannula and configured to house a proximal portion of the fiber; and a deflecting scanner, movably coupled to a distal end of the rotating scanner, configured to deflect a distal portion of the fiber, wherein the distal portion of the fiber is configured to emit and scan the guided light in a target region.

In another embodiment, a method of scanning with a scanning probe comprises operating a rotating scanner, rotatably positioned at least partially inside a cannula that extends from a proximal end of a handle, and configured to house a proximal portion of a fiber that is configured to receive a light from a light guide and to guide it to a distal end of the fiber; and operating a deflecting scanner, movably positioned at least partially inside the cannula and movably coupled to a distal end of the rotating scanner, the deflecting scanner being configured to deflect a distal portion of the fiber, wherein the distal portion of the fiber is configured to emit the guided light toward a target region, and the operating the rotating scanner and the deflecting scanner scans the emitted light across the target region.

DETAILED DESCRIPTION

This document describes embodiments of a scanning probe that address some of the above described problems as follows.

1. Some embodiments of the here-described scanning probes provide a two dimensional scanning capability without two counter-rotating cannulas. Such embodiments can be manufactured with a lower precision than probes with two rotating cannulas. In other words, the described embodiments have a lower tolerance for making the probe.

2. Some embodiments provide a more accurate and reliable 2D scanning operation. In particular, some embodiments can create the 2D scanning operation from a rotational scanning and a linear scanning, instead of two counter-rotating motions. As such, the operation of these embodiments is less sensitive for minor mismatches of the two types of scanning.

3. Switching to 1D scanning modes is natural and easy in some of these embodiments. In the described embodiments, disabling the rotational scanning immediately results in a linear scanning operation without the need of synchronizing two counter-rotating scanning motions.

4. Since embodiments do not require the accommodation of an outer and an inner cannula, the embodiments can be fabricated with a smaller, more compact form factor, or smaller diameter.

Some aspects of the embodiments consistent with the present disclosure have been disclosed in U.S. Provisional Patent Application No. 61/466,364, entitled "Pneumatically Driven Ophthalmic Scanning Endoprobe" by Michael J. Papac, Michael Yadlowsky, and John Huculak, filed on Mar. 22, 2011; in U.S. Provisional Patent Application No. 61/434,942, entitled "Counter-rotating Ophthalmic Scanner Drive Mechanism," by Michael Yadlowsky, Michael J. Papac, and John Huculak, filed on Jan. 21, 2011; in U.S. Provisional Patent Application Ser. No. 61/577,371, entitled "Reciprocating Drive Optical Scanner for Surgical Endoprobes" by Michael Yadlowsky, Michael J. Papac, and John C. Huculak, filed on Dec. 19, 2011; and in U.S. Provisional Patent Application 61/577,379, entitled "Concentric Drive Scanning Probe" by Michael Papac, John Huculak, and Michael Yadlowski, filed on Dec. 19, 2011. All four referenced patent applications are incorporated in their entirety herein.

Figure 1:
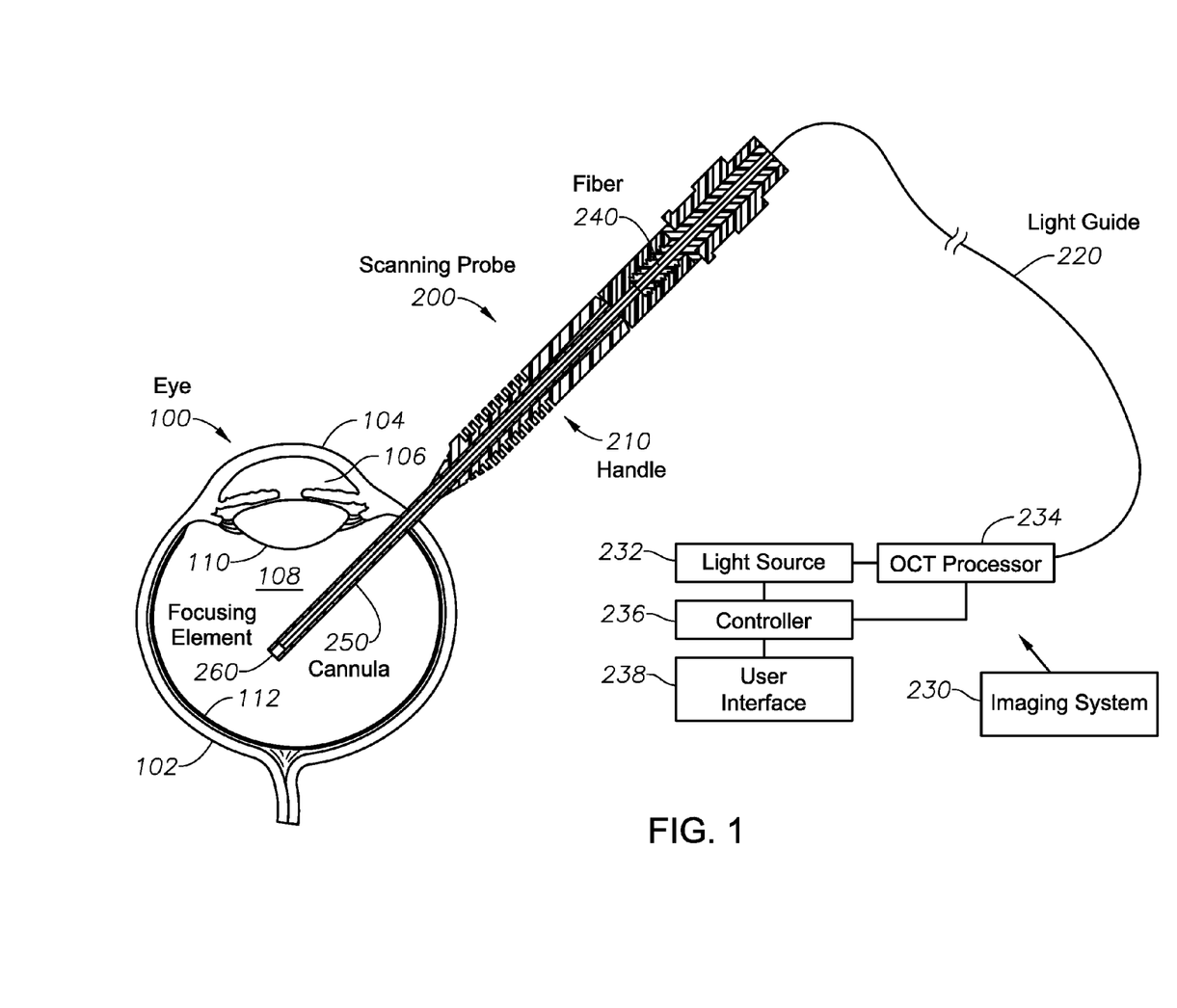
FIG. 1 illustrates a probe inserted into an eye.

FIG. 1 illustrates a general layout of an eye 100 and an optical scanning probe 200 according to some embodiments. The eye 100 typically includes a sclera 102, a cornea 104, an anterior chamber 106, a posterior chamber 108, and a lens 110 between the chambers 106 and 108. The distal inner surface of the eye 100 supports a retina 112. The scanning probes 200 are often inserted through an access hole, formed on the side, and away from the main optical axis of the eye 100, such as through the sclera 102, as shown.

The probe 200 can include a handle 210, formed to be gripped by an operator, such as a surgeon. A proximal end of the handle 210 can be coupled to a light guide 220 that is configured to guide a light from an imaging system 230. The handle 210 can be configured to receive a light beam from the light guide 220. In some handles 210, the light is received by a fiber 240. The fiber 240 can be a single mode or multi-mode optical fiber.

In some designs, a cannula 250 can protrude from a distal end of the handle 210. The fiber 240 can be positioned partially inside the handle 210 and partially inside the cannula 250. The fiber 240 can guide the light beam, received from the light guide 220 toward a distal end of the cannula 250.

Some scanning probes 200 include a focusing element 260 at the distal end of the cannula 250. Further, as mentioned above, some scanning probes can be coupled to the imaging system 230. Some embodiments of the imaging system 230 can include an Optical Coherence Tomography (OCT) system. OCT embodiments of the imaging system 230 split a light generated by a light source 232 into an imaging beam and a reference beam. The imaging beam can be guided to a target region by the light guide 220 and the fiber 240. The scanning probe 200 can collect the imaging light that is returned from the target region. Once the returned imaging light is guided back to the OCT imaging system 230, an OCT processor 234 can create an interference between the reference beam and the returned imaging beam and detect the interference. The OCT processor 234 can then create an in-depth image of the target region based on the detected interference. This in-depth, or OCT image provides the image of the target region in a range of depth for every point the imaging beam is directed to. An OCT image corresponding to a single point on the surface of the target region, such as the surface of the retina 112, is called an A-scan. In imaging systems that scan the imaging beam through a set of target points, the OCT image becomes a set or collection of A-scans, typically referred to as a B-scan. B-scans appear as cross sectional images of the target region, typically oriented in the XZ or YZ plane, where the X and Y directions are transverse to an optical axis of the probe 200, and the Z axis is parallel to the optical axis of the probe 200.

These operations can be performed under the control of a controller 236 and the results, including the OCT image, can be displayed through a user interface 238.

Without scanning the imaging beam, the OCT imaging system 230 is configured to create an A-scan. With scanning the imaging beam, the OCT imaging system is capable of generating a B-scan. The scanning can be performed by the surgeon manually, but in this case the calibrating of the image and the determination of the actual coordinates of the image points can lack precision. Scanning OCT images with much higher precision and calibration can be generated by scanning probes 200 that can scan the imaging beam in 1D or even in 2D.

Figure 2:
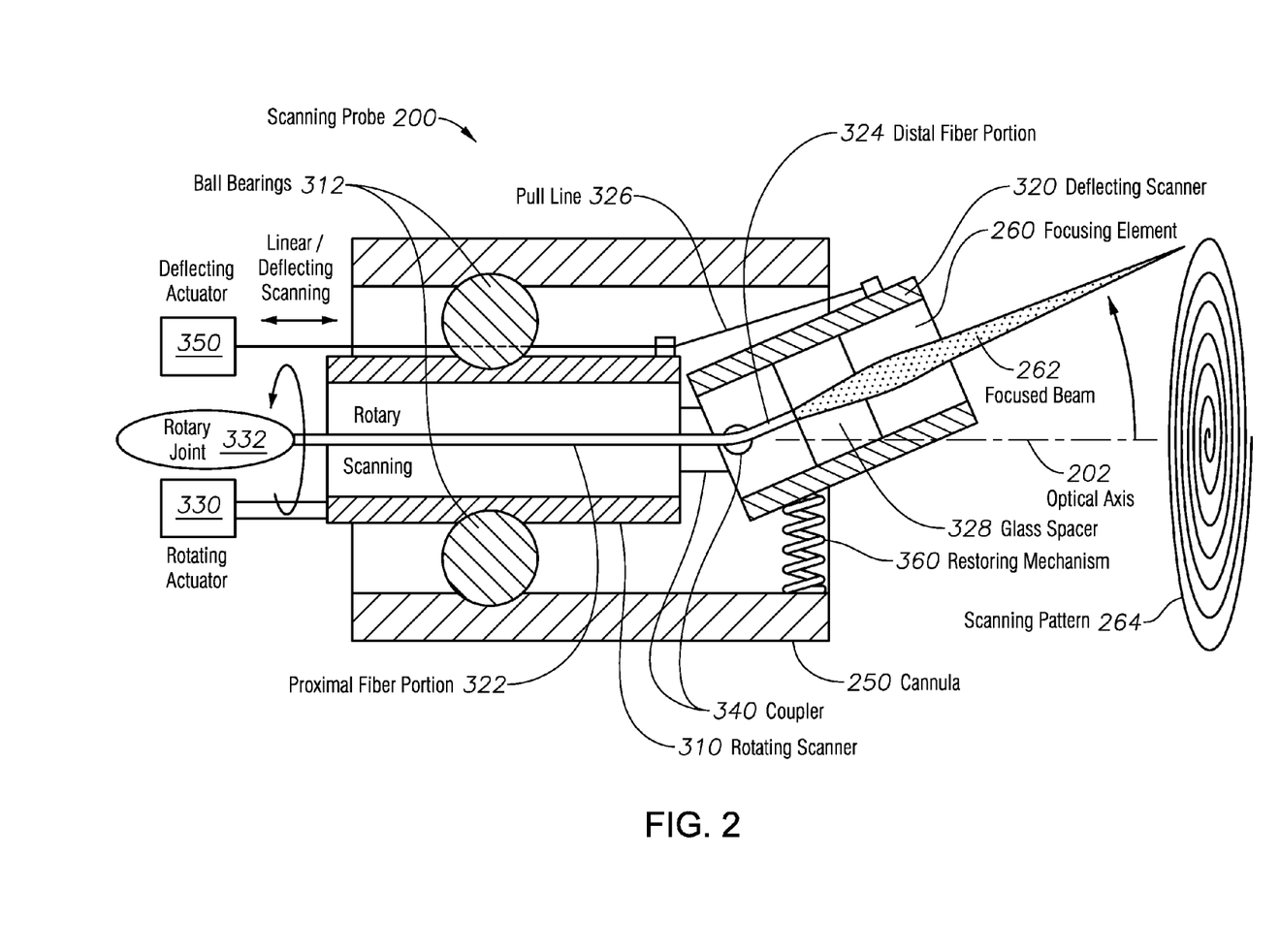
FIG. 2 illustrates an embodiment of a scanning probe.

FIG. 2 illustrates embodiments of the scanning probe 200 that are configured to scan the imaging beam in two dimensions (2D). The scanning probe 200 can include a rotating scanner 310, rotatably positioned at least partially inside the cannula 250 and configured to house a proximal fiber-portion 322 of the fiber 240. The scanning probe 200 can also include a deflecting scanner 320, movably positioned at least partially inside the cannula 250 and movably coupled to a distal end of the rotating scanner 310, configured to deflect a distal fiber-portion 324. The distal fiber-portion 324 is formed to emit the imaging beam, guided by the fiber 240 from the light guide 220. The emitted imaging beam can be focused into a focused beam 262 by a focusing element 260.

The deflecting scanner 320 can deflect the distal fiber-portion 324, thus scanning the guided imaging light in a target region. In detail, the deflecting scanner 320 can rotate around a transverse axis, thus bending, or deflecting the distal fiber-portion 324 in a transverse or lateral direction. The rotating scanner 310 can rotate this transverse axis. Therefore, the synchronized operation of the rotating scanner 310 and the deflecting scanner 320 can combine a rotational scanning and a linear scanning, as shown in FIG. 2, thus scanning the imaging light along 2D scan patterns in the target region.

Some scanning probes 200 can include a rotating actuator 330, configured to rotate the rotating scanner 310. The rotating actuator 330 can impart a rotating motion, or rotating scanning on the rotating scanner 310. The rotating actuator 330 can include a motor, a pneumatic rotator, a mechanical rotator, a piezoelectric system, or an electromagnetic rotator. The rotating actuator 330 can impart the rotating scanning by, e.g., a gear assembly or a torque cable, rotating a cannula of the rotating scanner 310. The rotational scanning of the rotating scanner 310 can be assisted by optional ball bearings 312.

In some scanning probes 200, the deflecting scanner 320 can include a transverse scanner, a lateral scanner, a radial scanner, or an angular scanner. The deflecting scanner 320 can be movably coupled to the rotating scanner 310 by a coupler 340 that can include a hinge, a pivot, a flexible cannula, a connecting cannula, a joint, or a connector.

The scanning probe 200 can include a deflecting actuator 350 to deflect the deflecting scanner 320. The deflecting actuator 350 can impart a linear motion, linear scanning, or deflecting scanning on the deflecting scanner 320. The deflecting actuator 350 can include a rotational motor, a linear motor, a pneumatic actuator, an energizable electric coil, a piezoelectric actuator, a piezoelectric cantilever, a micro-electromechanical (MEMS) system, an electrostatic actuator, or a fiber bundle.

In the shown embodiment, the deflecting actuator 350 imparts the deflecting scanning on the deflecting scanner 320, in other words, actuates the deflecting scanner 320, by pulling a pull-line 326, coupled to the deflecting scanner.

In other embodiments, the deflecting actuator 350 can impart the linear motion on the deflecting scanner 320 by moving a pushrod to actuate the deflecting scanner.

In some scanning probes 200, the deflecting scanner 320, the deflecting actuator 350, or both, can comprise a restoring mechanism 360, such as a reset mechanism, a return mechanism, a spring loaded mechanism, an elastic cannula, a flexible element, an electrostatic mechanism, or a memory alloy.

The restoring mechanism 360 can counteract the actuation of the pull-line 326 by restoring the deflecting actuator 320 to an equilibrium, or neutral position, such as aligned with an optical axis 202 of the scanning probe 200.

Figure 3:
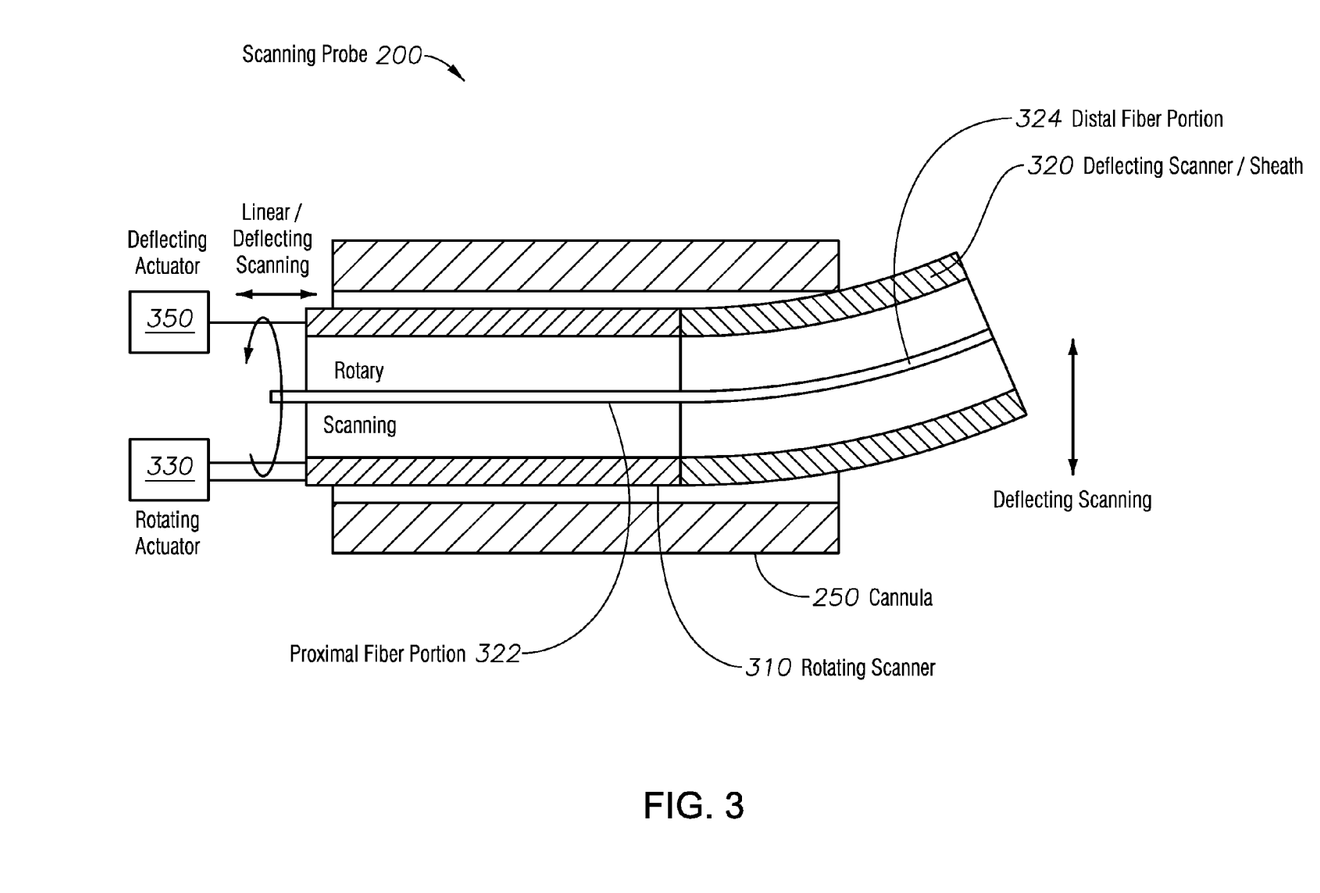
FIG. 3 illustrates another embodiment of a scanning probe.

FIG. 3 illustrates that in some embodiments of the scanning probe 200, the deflecting scanner 320 comprises a distally bent sheath, configured to house the distal fiber-portion 324. The sheath 320 can include a flexible material or a memory alloy. In these embodiments, the deflecting actuator 350 can move the deflecting scanner/sheath 320 in a linear forward-backward manner. In some cases this can be achieved by forming an assembly from the rotating scanner/cannula 310 and the deflecting scanner/sheath 320, and moving this assembly in the linear manner. This can move the distally bent flexible sheath 320 relative to a constraining structure, such as the cannula 250. As shown in FIG. 3, the forward-backward motion forces the flexible sheath 320 to bend up and down, thus scanning the distal fiber-portion 324 linearly or in a deflecting pattern.

In various embodiments of the scanning probe 200, such as in the embodiments of FIGS. 2 and 3, the deflecting scanner 320 can be configured to deflect the distal fiber-portion 324 from the optical axis 202 of the cannula 250 up to a maximum deflection angle. The maximum deflection angle can be 30, 45, 60, or 90 degrees.

In some embodiments of the scanning probe 200, the proximal fiber-portion 322 or the distal fiber-portion 324 can be able to rotate relative to at least one of the rotating scanner 310 and the deflecting scanner 320. Such embodiments can reduce or avoid altogether a torsional deformation of the fiber 240 during scanning.

In some embodiments of the scanning probe 200, the proximal fiber-portion 322 can be affixed non-rotationally to the rotating scanner 310, or the distal fiber-portion 324 can be affixed non-rotationally to the deflecting scanner 320. These non-rotational connections may keep the distal fiber-portion 324 in a defined alignment with the focusing element 260, thus improving an optical performance of the scanning probe 200. At the same time, in these embodiments where a fiber-portion is non-rotationally affixed to the rotating scanner 310 or to the deflecting scanner 320, the rotational scanning can torque the fiber 240, since the non-rotationally affixed fiber-portion is actually rotating relative to the light guide 220 during the rotational scanning To reduce or eliminate this torque, some scanning probes 200 can include a rotary joint 332, positioned between the non-rotationally affixed fiber-portion and the light guide 220, as shown in FIG. 2.

In some embodiments of the scanning probe 200, the rotating scanner 310 can rotate uni-directionally or bi-directionally. Scanning with a bi-directional (back-and-forth) rotation can reduce torqueing the fiber 240 that can be useful in embodiments where a fiber-portion is affixed non-rotationally to a scanner.

In some embodiments of the scanning probe 200, the focusing element 260, positioned distally to the distal fiber-portion 324 at a distal region of the cannula 250 can include a Gradient Index of refraction, or GRIN, lens. In some embodiments, the distal fiber-portion 324 can be affixed to a proximal portion of the focusing element 260. In some cases, this is achieved by fusion splicing. Finally, in some designs, the distal fiber-portion 324 is coupled to a glass spacer, or spacing element 328 that is attached to the focusing element 260.

FIGS. 4A-D illustrate that the scanning probe 200 can scan the beam 262 along a 2D pattern 264 by synchronizing a rotating, or rotational scanning, actuated by the rotating actuator 330, and a deflecting scanning, actuated by the deflecting actuator 350 in a designed relationship.

Figure 4A:
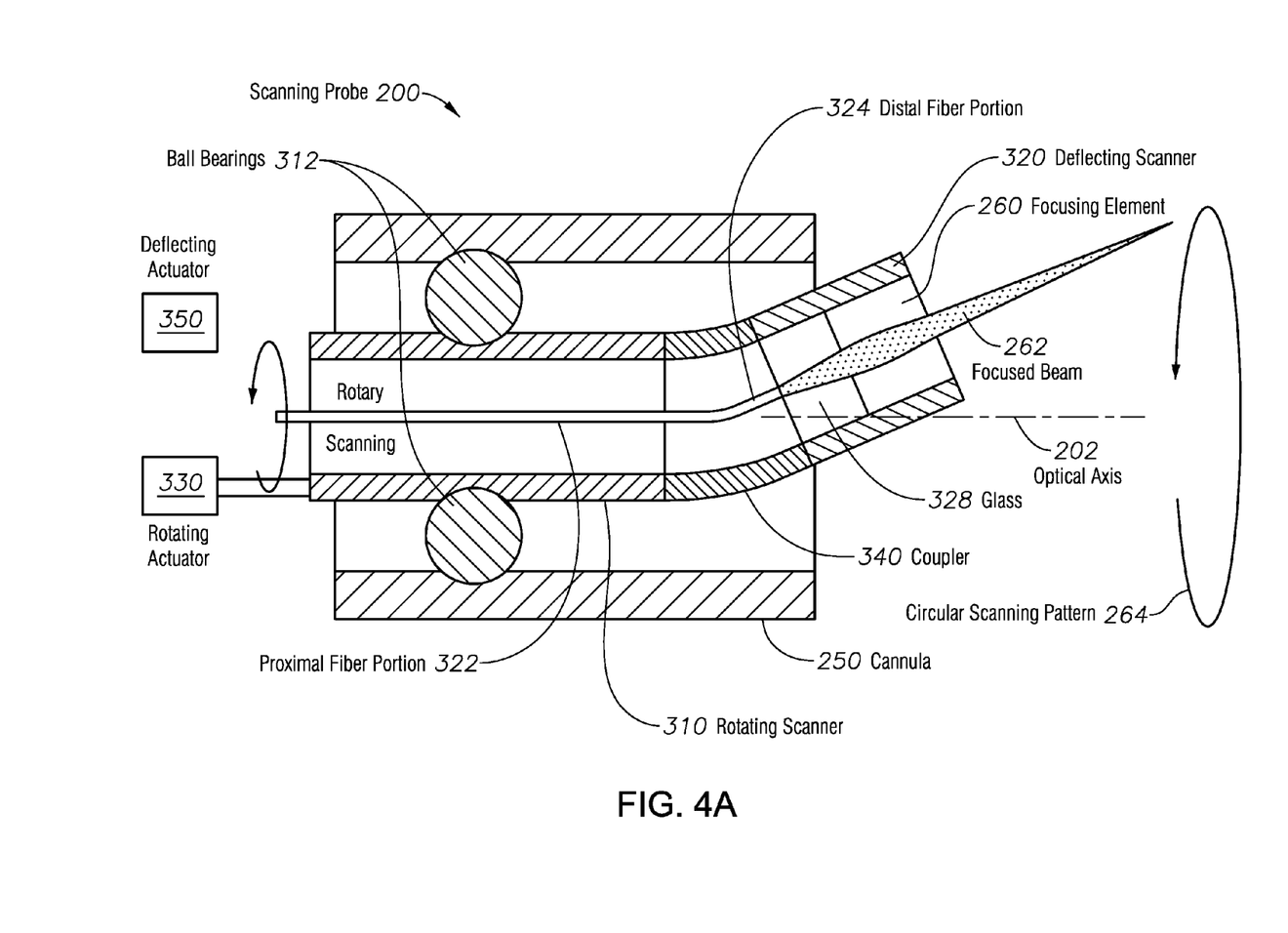
FIG. 4A-D illustrate types of scanning actuation of a scanning probe.

FIG. 4A illustrates the case when the deflecting actuator 350 does not actuate a linear or deflecting scanning, thus the only actuation is that of the rotating actuator 330, causing a rotational scanning that scans the focused beam 262 along a circular scanning pattern 264.

Figure 4B:
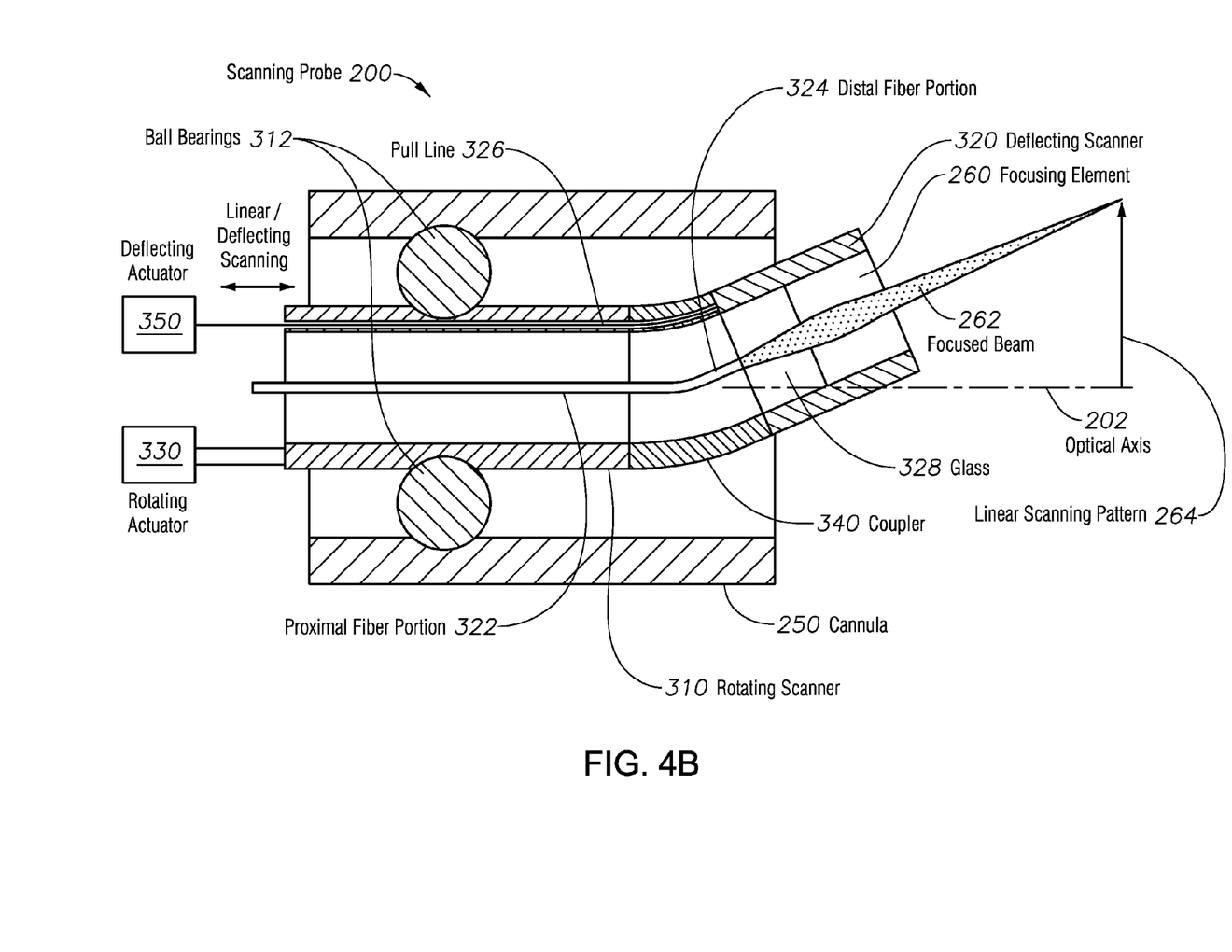

FIG. 4B illustrates the complementary case when the rotating actuator 330 does not actuate a rotating scanning, thus the only actuation is that of the deflecting actuator 350, causing a deflecting scanning that scans the focused beam 262 along a linear scanning pattern 264.

Figure 4C:
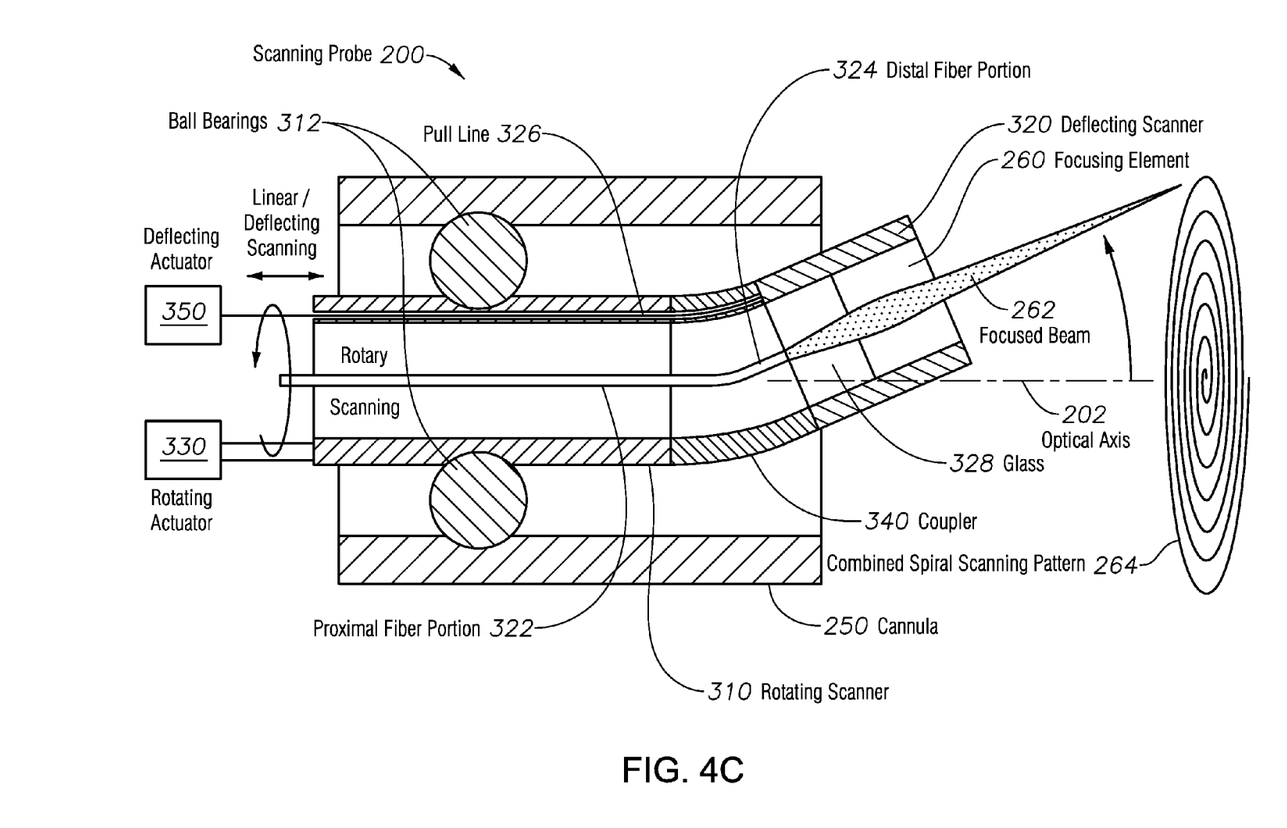

FIG. 4C finally illustrates that when the rotational scanning actuated by the rotating actuator 330 is synchronized with the linear, or deflecting, scanning actuated by the deflecting actuator 350, a wide variety of 2D scanning patterns 264 can be scanned with the beam 262, such as the shown spiral scanning pattern 264.

Figure 4D:
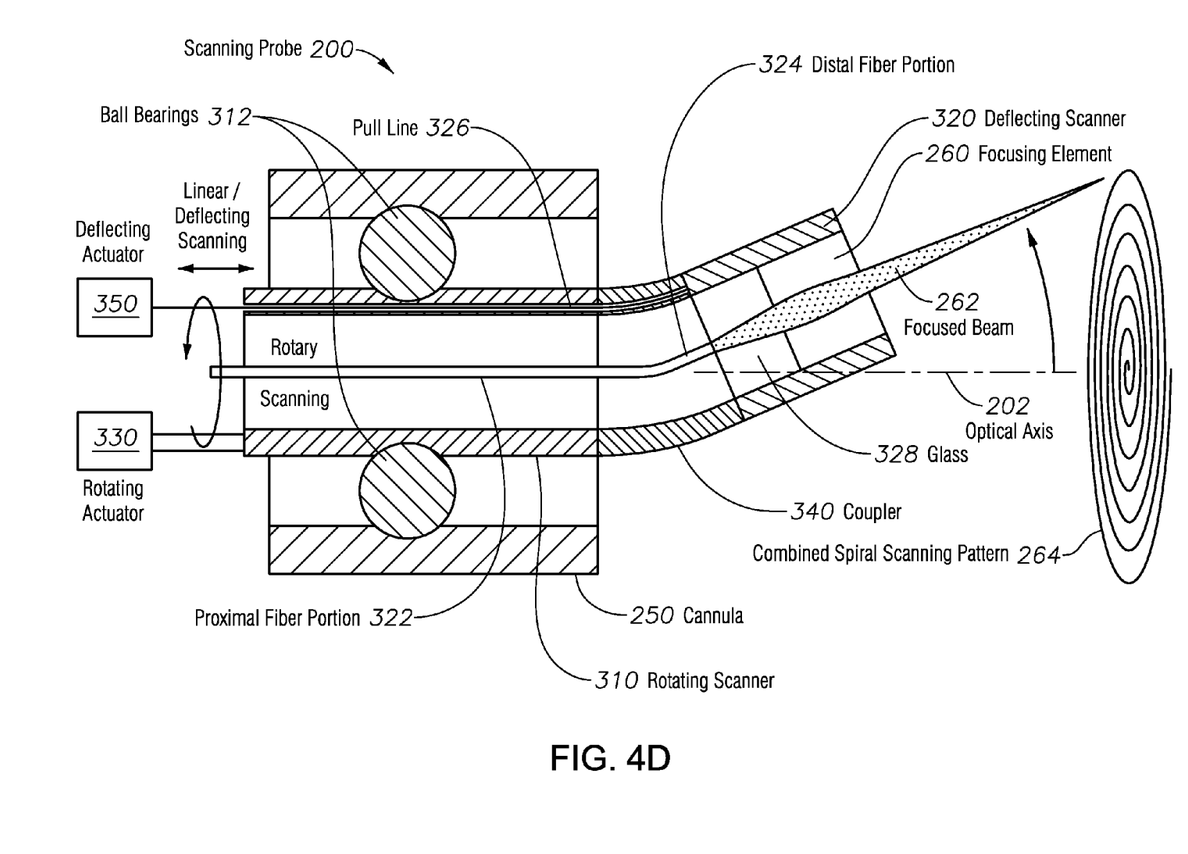

Finally, FIG. 4D illustrates that while in the embodiments of FIGS. 4A-C the deflecting scanner 320 can be positioned partially inside the cannula 250, in other embodiments, the deflecting scanner 320 can be positioned completely distally and outside the cannula 250.

Figure 5A:
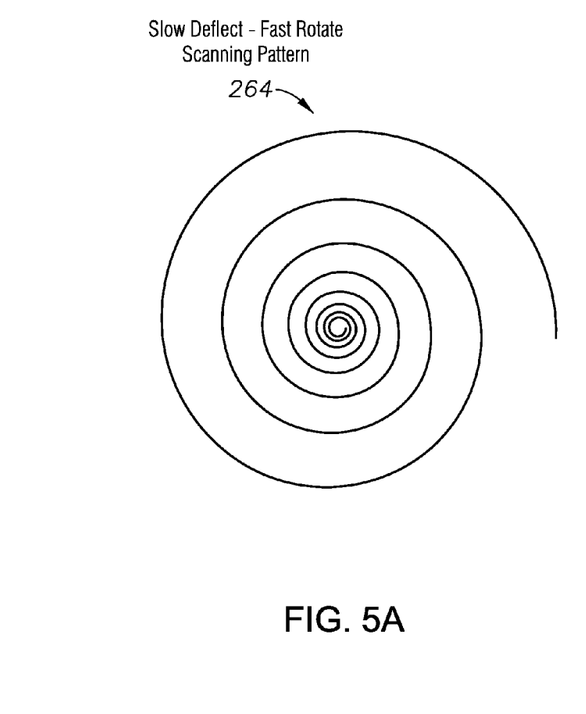
FIGS. 5A-B illustrate scanning patterns.
Figure 5B:
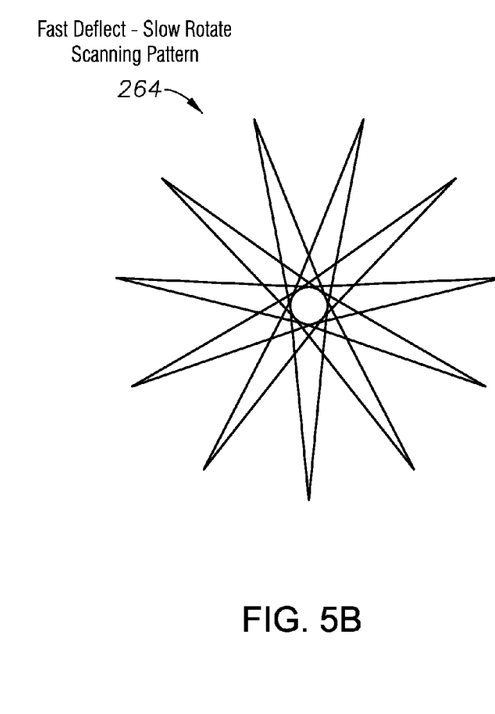

FIGS. 5A-B illustrate other forms of synchronization between the two scanning actuations, resulting in different scanning patterns 264.

FIG. 5A illustrates the case when the designed relationship is such that a period of the rotating is faster than a period of the deflecting. This relationship of the scanning periods scans the beam 262 along the previously described spiral scanning pattern 264.

FIG. 5B illustrates the case when the designed relationship is such that a period of the rotating is slower than a period of the deflecting. This relationship of the scanning periods scans the focused beam 262 along a star-like scanning pattern 264. In either of the above embodiments of FIGS. 5A-B, at least one of a period of the rotating and a period of the deflecting can be in at least one of the ranges of 0-10 Hz, 0-100 Hz, 0-1 kHz, 0-10 kHz and 0-100 kHz.

Each of these ranges can have its own advantages for various applications. These applications include the scanning probe 200 being part of an optical coherence tomography imaging system, a surgical tool, a two photon imaging system, a multi-photon imaging system, a fluorescent imaging system, a scanning panretinal photocoagulation system, or a beam delivery system.

In embodiments, when the scanning probe 200 is part of, or coupled to an OCT imaging system 230, the scanning probe 200 can receive a returned emitted light, returned from the imaging target region, and forward the received light to the OCT imaging system 230.

In some embodiments, a method of scanning with a scanning probe can include: (a) operating a rotating scanner, rotatably positioned at least partially inside a cannula that extends from a proximal end of a handle, and configured to house a proximal portion of a fiber that is configured to receive a light from a light guide and to guide it to a distal end of the fiber; and (b) operating a deflecting scanner, movably coupled to a distal end of the rotating scanner, the deflecting scanner being configured to deflect a distal portion of the fiber. Here, the distal portion of the fiber can be configured to emit the guided light toward a target region, and the operating the rotating scanner and the deflecting scanner scans the emitted light across the target region.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately, or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. An optical scanning probe, comprising:
a handle, configured to receive a light beam from a light guide;
a cannula, extending from a distal end of the handle;
a fiber, positioned partially inside the handle and partially inside the cannula, configured to guide the received light beam toward a distal end of the cannula;
a rotating scanner, rotatably positioned at least partially inside the cannula and configured to house a proximal portion of the fiber; and
a deflecting scanner, movably coupled to a distal end of the rotating scanner, configured to deflect a distal portion of the fiber,
wherein the distal portion of the fiber is configured to emit and scan the guided light in a target region.

2. The scanning probe of claim 1, comprising:
a rotating actuator, configured to rotate the rotating scanner,
wherein the rotating actuator comprises at least one of a motor, a pneumatic rotator, a mechanical rotator, a piezoelectric system and an electromagnetic rotator.

3. The scanning probe of claim 1, the deflecting scanner comprising at least one of:
a transverse scanner, a lateral scanner, a radial scanner, and an angular scanner.

4. The scanning probe of claim 1, wherein:
the deflecting scanner is configured to rotate around a transverse axis.

5. The scanning probe of claim 1, comprising:
a coupler, configured to movably couple the deflecting scanner to the rotating scanner, the coupler comprising at least one of a hinge, a pivot, a flexible cannula, a connecting cannula, a joint and a connector.

6. The scanning probe of claim 1, comprising:
a deflecting actuator, configured to deflect the deflecting scanner,
wherein the deflecting actuator comprises at least one of a rotational motor, a linear motor, a pneumatic actuator, an energizable electric coil, a piezoelectric actuator, a piezoelectric cantilever, a microelectromechanical system, an electrostatic actuator and a fiber bundle.

7. The scanning probe of claim 6, wherein:
the deflecting actuator is configured to actuate the deflecting scanner by pulling a pull-line, coupled to the deflecting scanner.

8. The scanning probe of claim 6, wherein:
the deflecting actuator is configured to actuate the deflecting scanner by moving a pushrod to actuate the deflecting scanner.

9. The scanning probe of claim 6, wherein:
at least one of the deflecting scanner and the deflecting actuator comprises a restoring mechanism, comprising at least one of a reset mechanism, a return mechanism, a spring loaded mechanism, an elastic cannula, a flexible element, an electrostatic mechanism and a memory alloy.

10. The scanning probe of claim 6, wherein:
the deflecting scanner comprises a distally bent sheath, configured to house the distal portion of the fiber and comprising at least one of a flexible material and a memory alloy; and
the deflecting actuator is configured to cause the relative movement of the distally bent flexible sheath and a constraining structure.

11. The scanning probe of claim 1, wherein:
the deflecting scanner is configured to deflect the distal portion of the fiber from an optical axis of the cannula up to a maximum deflection angle, wherein the maximum deflection angle is one of 30, 45, 60, and 90 degrees.

12. The scanning probe of claim 1, wherein:
a portion of the fiber is configured to be able to rotate relative to at least one of the rotating scanner and the deflecting scanner.

13. The scanning probe of claim 1, wherein:
at least one of the proximal portion of the fiber is affixed non-rotationally to the rotating scanner, and the distal portion of the fiber is affixed non-rotationally to the deflecting scanner.

14. The scanning probe of claim 13, wherein:
a rotary joint is positioned between the non-rotational affixed portion of the fiber and the light guide.

15. The scanning probe of claim 1, wherein:
the rotating scanner is configured to rotate at least one of uni-directionally and bi-directionally.

16. The scanning probe of claim 1, comprising:
a focusing element, positioned distally to the distal portion of the fiber at a distal region of the cannula.

17. The scanning probe of claim 16, wherein:
the distal portion of the fiber is affixed to a proximal portion of the focusing element.

18. The scanning probe of claim 1, wherein:
the probe comprises a rotating actuator and a deflecting actuator; and
the probe is configured such that a rotating actuated by the rotating actuator and a deflecting actuated by the deflecting actuator are synchronized in a designed relationship.

19. The scanning probe of claim 18, wherein:
the designed relationship is one of a period of the rotating is slower than a period of the deflecting, and a period of the rotating is faster than a period of the deflecting.

20. The scanning probe of claim 1, wherein:
at least one of a period of the rotating and a period of the deflecting is in at least one of the ranges of 0-10 Hz, 0-100 Hz, 0-1 kHz, 0-10 kHz and 0-100 kHz.

21. The scanning probe of claim 1, wherein:
one of the rotating scanner and the deflecting scanner can be operated when the other scanner is not being operated.

22. The scanning probe of claim 1, wherein:
the probe does not contain two counter-rotating scanners.

23. The scanning probe of claim 1, wherein:
the probe is configured to receive a returned emitted light, returned from an imaging target, and to forward the received light to an imaging system.

24. The scanning probe of claim 1, wherein:
the scanning probe is part of at least one of an optical coherence tomography system, a surgical tool, a two photon imaging system, a multi-photon imaging system, a fluorescent imaging system, a scanning panretinal photocoagulation system, and a beam delivery system.

25. The scanning probe of claim 1, wherein the fiber comprises the proximal portion and the distal portion, wherein the distal portion is deflectable relative to the proximal portion.

26. The scanning probe of claim 25, wherein the deflecting scanner is movable to an oblique angle relative to the rotating scanner such that the distal portion of the fiber is deflectable to the oblique angle relative to the proximal portion of the fiber.

27. A method of scanning with a scanning probe, the method comprising:
   operating a rotating scanner, rotatably positioned at least partially inside a cannula that extends from a proximal end of a handle, and configured to house a proximal portion of a fiber that is configured to receive a light from a light guide and to guide it to a distal end of the fiber; and
   operating a deflecting scanner, movably coupled to a distal end of the rotating scanner, the deflecting scanner being configured to deflect a distal portion of the fiber,
   wherein the distal portion of the fiber is configured to emit the guided light toward a target region, and the operating the rotating scanner and the deflecting scanner scans the emitted light across the target region.

* * * * *